United States Patent [19]

Giampapa et al.

[11] Patent Number: 4,502,484
[45] Date of Patent: Mar. 5, 1985

[54] NASAL SURGICAL SAW

[76] Inventors: Vincent C. Giampapa, 444 Central Park W., New York, N.Y. 10027; George C. Peck, 1200 Rte. 46, Clifton, N.J. 07013

[21] Appl. No.: 501,428

[22] Filed: Jun. 6, 1983

[51] Int. Cl.³ ............................................. A61B 17/14
[52] U.S. Cl. ..................................... 128/317; 30/355; 30/356; 30/393
[58] Field of Search ............. 128/317; 30/166 R, 392, 30/393, 355, 356

[56] References Cited

U.S. PATENT DOCUMENTS

| | | | |
|---|---|---|---|
| 1,359,870 | 11/1920 | Buckland | 30/356 X |
| 1,769,400 | 7/1930 | Talmage | 30/166 |
| 2,741,248 | 4/1956 | Woodhall | 128/317 |
| 2,951,482 | 9/1960 | Sullivan | 128/317 |
| 4,036,236 | 7/1977 | Rhodes, Jr. | 128/317 |

Primary Examiner—William H. Grieb
Attorney, Agent, or Firm—M. K. Silverman; J. A. Giampapa

[57] ABSTRACT

A surgical saw including a shank extension is adapted for securement within a reciprocating power handle held within the hand of a surgeon. The saw comprises an elongated, concave, curved, relatively thin blade, the blade having X-, Y-, and Z- axes, the concave curve of the blade beginning on the X-axis at about 60% of the length thereof while turning into the Z-axis and, at about 80% of the length of said blade, also turning into the Y-axis, wherein the concave curve of the blade will thereby follow the anatomic curve of the nasal-maxillary junction, the blade also defining a plurality of cutting teeth along the inferior cross-sectional edge of the XY plane of such teeth.

5 Claims, 8 Drawing Figures

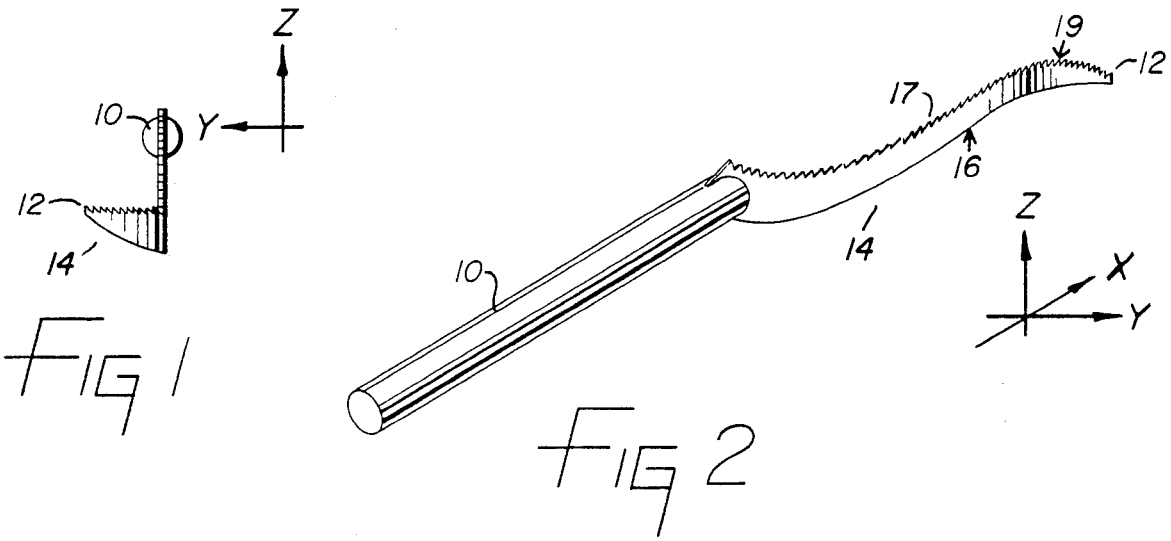
Fig 1
Fig 2
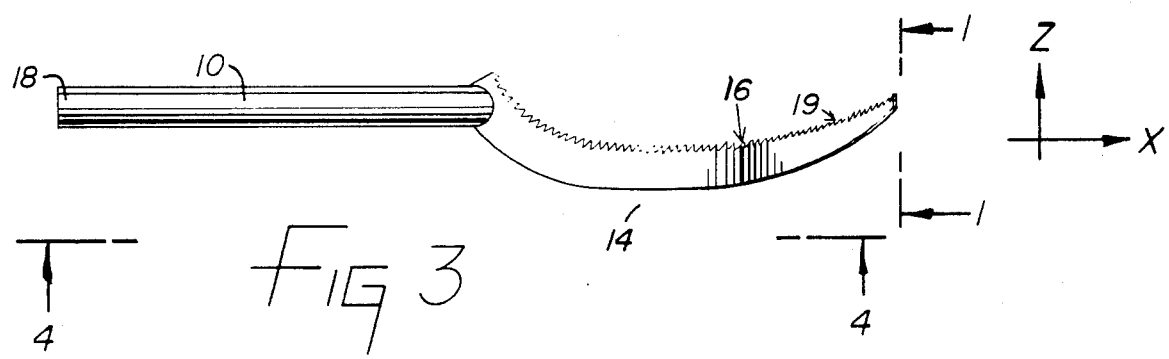
Fig 3
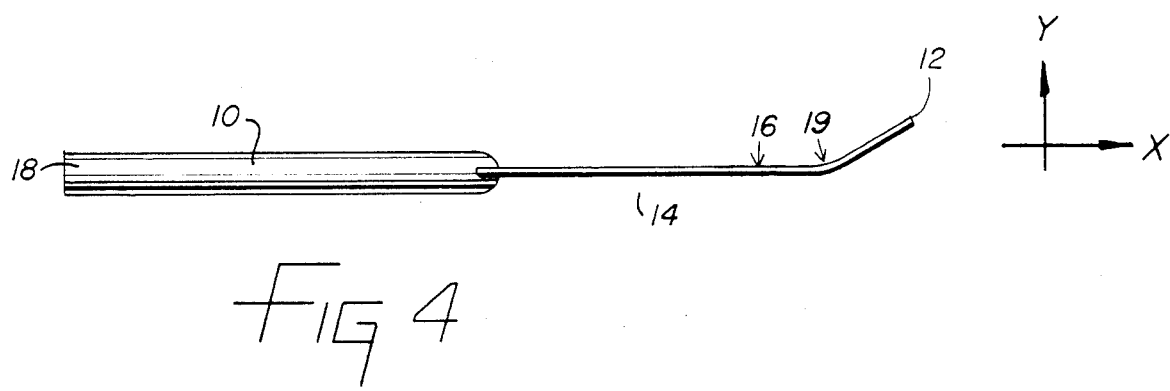
Fig 4

NASAL SURGICAL SAW

BACKGROUND OF THE INVENTION

This invention relates generally to cutting tools and, more particularly, to a cutting saw used by surgeons in the course of nasal surgery.

In the past, surgical instruments of the type herein involved have been constructed generally along the lines of a scalpel, utilizing the same type of straight, smooth handle members, with teeth being formed similar to those of a rasp or the like. Alternatively, surgeons involved in nasal surgery have made use of a hammer and chisel in order to reduce or change the dimensions or slope of the nasal bone or nasal maxillary junction.

In both situations, the principal cutting or reducing action is accomplished when the instrument used is pushed by the hand of the surgeon in a direction against the nasal bone, towards the orbital cavity and, then, away from the orbital cavity. Such manual pushing action may be quite dangerous, particularly in the cutting of bone from the nasal passages in which a slip of the saw or chisel can easily result in the penetration of the orbital cavity, with possibly serious consequences. It will also be appreciated that in the course of an operation, the surgeon's rubber gloves and, thus, the handles of the instruments used, may be covered with blood, thereby increasing the possibility of slippage or other accidents.

A further problem in the area of nasal surgery has been the difficulty in attaining a sure and reliable reduction of the nasal bone. More particularly, the peculiar anatomy of the nasal-maxillary junction has been an historically difficult one to accurately operate upon, as has been the nasal bone proper. Today most surgeons still perform rhinoplasties using the traditional hammer and chisel method in order to accomplish reduction of the thick portion of the nasal bone. This method has, over the years, been proven to be notoriously difficult to maneuver in, with presently available instruments. Accordingly, the present invention may be viewed as a response to the above-described longstanding problems that have existed in the prior art.

The most pertinent prior art known to the inventors is U.S. Pat. No. 2,741,248 to Woodhall; U.S. Pat. No. 2,951,482 to Sullivan; and U.S. Pat. No. 4,036,236 to Rhodes.

SUMMARY OF THE INVENTION

The instant invention is directed to a surgical saw including a shank extension adapted for securement within a reciprocating power handle held within the hand of a surgeon. The saw comprises an elongated, concave, curved, relatively thin blade, said blade having X-, Y-, and Z-axes, the concave curve of said blade beginning on said X-axis at about sixty percent of the length while turning into the Z-axis and, at about eighty percent of the length of said blade, also turning into the Y-axis, wherein said concave curve of said blade will thereby follow the anatomic curve of the nasal-maxillary junction, said blade also defining a plurality of cutting teeth along the inferior cross-sectional edge of the XY plane of such teeth.

It is an object of the present invention to provide a blade for use in cosmetic and reconstructive nasal surgery of the nasal bone thereby facilitating more effective surgery in connection therewith.

It is a further object to provide a nasal saw particularly suitable for use in rhinoplasty procedures and in surgery of both the thin and thick portions of the nasal bone.

It is a yet further object to provide a surgical saw that will enhance the safety factors associated with surgery of the nasal area.

It is a still further object to provide a nasal saw which will make possible a greater degree of precision in rhinoplasty operations, decreasing the chance of incomplete fractures, of comminution of the nasal bone, and of step-off deformities.

The above and yet further objects will become apparent from the hereinafter set forth Detailed Description of the Invention, the Drawings, and Claims as appended herewith.

BRIEF DESCRIPTION OF THE DRAWINGS

FIG. 1 is a perspective view of the inventive nasal saw taken along the front X-axis thereof.

FIG. 2 is an isometric view of the invention.

FIG. 3 is a longitudinal view of the nasal saw, taken in the XZ plane thereof.

FIG. 4 is a longitudinal view of the nasal saw, taken in the XY plane thereof.

DETAILED DESCRIPTION OF THE INVENTION

Figure 5:
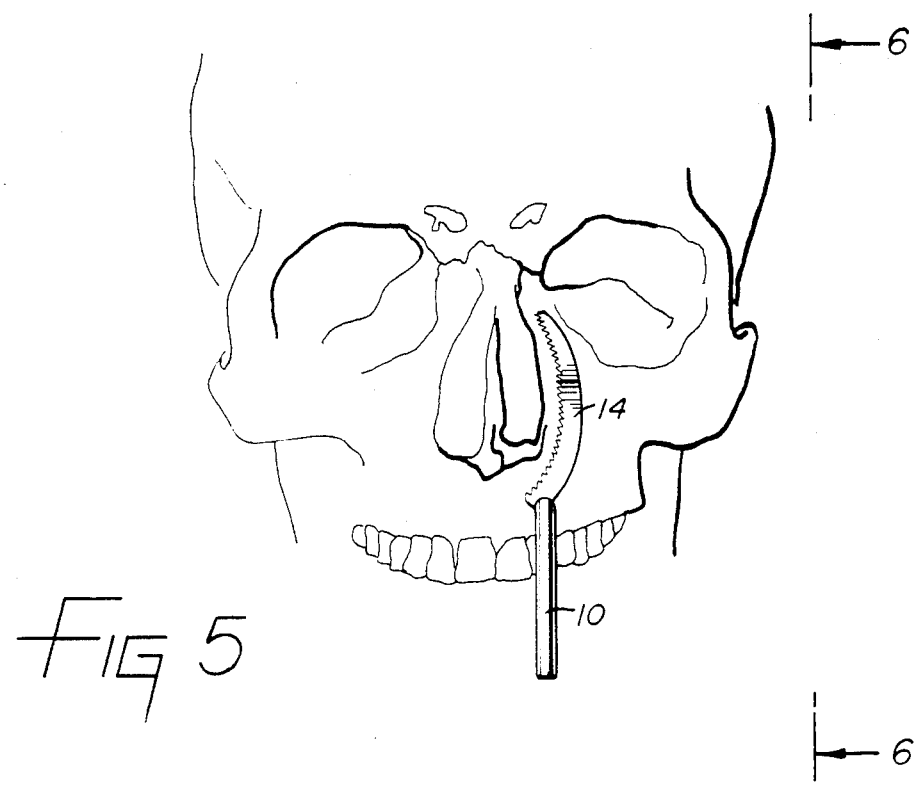
FIG. 5 is a front schematic view of the nasal and orbital areas of the facial skeleton, showing the relationship of the contour of the nasal bone to that of the saw.

In FIG. 1 is shown a perspective view of the inventive nasal saw taken along the front X-axis thereof. More particularly, in FIG. 1, there may be seen a shank extension 10 which is suitable for securement within a reciprocating power handle 20 (see FIG. 8) which is held within the hand of a surgeon. A connecting end 18 of the shank extension 10 is held within a chuck 24 of the power handle 20.

It is noted that the shank extension 10 is in the nature of a cylindrical segment having its longitudinal characteristic within the X-axis. See FIG. 2. A tip (second end) 12 of a blade 14 is also shown in FIGS. 1 and 2. It is noted that the blade 12 integrally depends from the shank extension 10.

In the isometric view of FIG. 2, characteristics of the nasal saw may be seen in all three dimensions. More particularly, the "lazy S" characteristics of the blade, which is concave in both the XY and XZ planes, can be seen. Through the view of FIG. 2, it may be appreciated that the blade does not turn from its longitudinal X-axis into the Z-axis until approximately 60% of its length as measured from the first end of the blade, i.e., that end at which the integral dependancy of the blade from the shank extension commences. Such turn from the longitudinal X-axis into the Z-axis is indicated by point 16 in FIGS. 2, 3 and 4. Thereafter, the blade, at about 80% of its length from the first end of the blade, also turns into the Y-axis. The point of commencement of this XY curve is indicated by point 19 in FIGS. 2, 3 and 4.

With more particular reference to FIG. 3, the blade is illustrated in the XZ plane and, therein, it may be clearly noted that the blade does not turn from the longitudinal X-axis into the Z-axis until approximately 60% of its length, that is, at point 16. Similarly, in FIG. 4, the blade is particularly illustrated in the XY plane and, therein, it may be noted that the blade does not turn from the longitudinal X-axis into the Y-axis until approximately 80% of its length from the first end of such blade, that is, at point 19.

The particular geometry apparent in FIGS. 2, 3 and 4 is dictated by the requirement that the concave curve of the blade follow the anatomical curve of the nasal-maxillary junction of the nose. As will be hereinafter set forth, this particular curvature is necessary in order to provide a surgical saw suitable for the intended use.

It is also noted that the blade is typically formed of stainless steel having a Y-axis thickness of 0.5 mm, while the main Z-axis width of the blade is about 4 mm. Further, the X-axis length of the blade is preferably in the neighborhood of 30 mm.

Figure 6:
FIG. 6 is a side schematic view of the nasal and orbital areas of the facial skeleton showing the manner of insertion and cutting position of the blade on the nasal bone.
Figure 7:
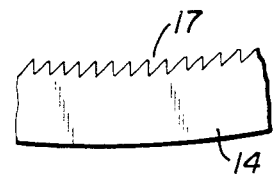
FIG. 7 is an enlarged view of the structure of the cutting teeth.

The anatomical situation with reference to the facial skeleton and surrounding soft tissue in the nasal, maxillary and orbital areas is shown schematically in FIGS. 5 and 6. FIG. 5 illustrates, in front view, the normal shape of the nasal-maxillary junction in the Caucasian racial group. The shape of this junction will differ somewhat for other racial groups, in which case it is to be appreciated, suitable variations in the extent of the Z-axis curvature of the blade (see FIG. 3) would be indicated. The nasal-maxillary junction is referred to by some facial surgeons as a lazy S-curve. Accordingly, the geometry of the present surgical nasal saw is intended to conform, as nearly as is practical, to the S-curve of the edge of the nose. Further, it is to be appreciated that the blade will be produced, packaged, and used by facial surgeons as a pair, in which one blade is provided for surgery on the left side of the nose, while a second blade is provided for surgery upon the right side of the nose. It is, therefore, to be understood that the various Y- and Z-axis curvatures are shown and described with reference to FIGS. 3 and 4 respectively are reversed as to the respective Y- and Z-axes for the purposes of the complementary saw employed for use upon the opposite side of the nose.

Conceptually, the surgical nasal saw and its use are predicated upon two concepts, namely, that the cutting edge exhibits a three-dimensional curvature, permitting it to conform to the natural shape of the sides of the nasal bone, thereby allowing the surgeon to simultaneously cut the nasal bone along its entire length. This concept differs markedly from prior art practice in which the use of a straight blade, not having a concave surface, rendered it necessary for the surgeon to cut deeply into the nasal cavity before cutting the superior portion of the nasal bone, and thereafter, to cut one segment at a time. The other concept of the present invention is that the blade is elevated or curved in its lateral dimensions so as to avoid damage to the orbital area or to the suspensionary ligamental portion about the eyes. Therefore, with the present blade, it is possible and practical to bring the nasal cut up from the nasal cavity along the junction of the thin and thick portions of the nasal bone. This is schematically shown in FIG. 6 in which the inserted blade is shown underneath the soft tissue in an upward cutting position along the nasal-maxillary junction. Also shown in FIG. 6 is the 30 degree offset of the Z-axis curve of FIG. 3. It has been discovered that such a 30 degree Z-axis incline is the most practical curvature for purposes of surgery involving the nasal-maxillary junction.

With further reference to FIGS. 3 and 6, it is seen that control 22 of the power handle 20 is selectively depressed in order to reciprocate the blade 14 in the YZ plane and thereby accomplish the desired cutting along the nasal-maxillary junction.

Figure 8:
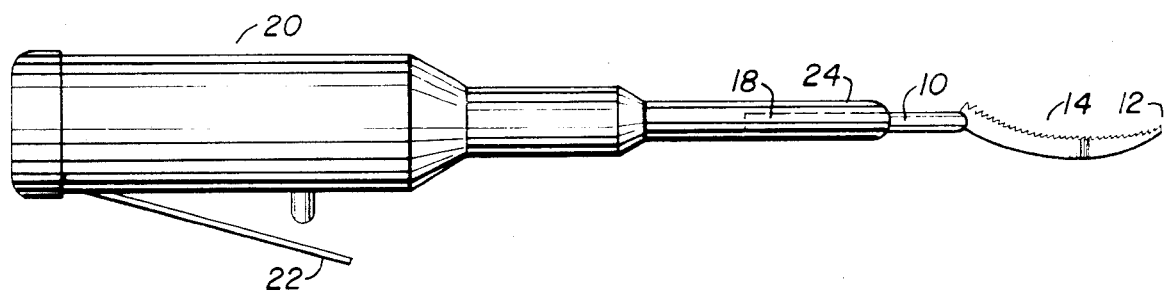
FIG. 8 is a perspective view of the saw, saw handle and saw chuck in the XY plane.

With reference to FIG. 8, there is illustrated a reciprocating power handle 20 which is constructed to be grasped in the hand of the surgeon. Integrally communicating with said handle 20 is a shank 10 and, therefrom, the elongated, concave, curved, relatively thin blade 14.

Shown in FIG. 8 is the entire solid round shank 10 which can be provided at its proximate end 18 with means 24 to adjust the distance from the power handle 20 to the nostril and soft tissue of the nose. Also, the first end 12 of the blade 14 is provided with blunt corners to avoid soft tissue damage.

While there have been shown and described the preferred embodiments of the invention, it will be understood that the invention may be embodied otherwise than as may be herein illustrated or described, and that within such embodiments certain changes in the detail or construction, or in the form and arrangements of the parts, may be made without departing from the underlying idea or principles of this invention in the scope of the appended claims.

Having thus described our invention, what we claim as new, useful and non-obvious and, accordingly, secure by Letters Patent of the United States is:

1. A surgical saw including a shank extension suitable for securement within a reciprocating power handle held and operated within the hand of a surgeon, the surgical saw comprising:
    (a) a first end and a second end, said first end integrally depending from said shank extension; and
    (b) an elongated, concave, curved, thin blade, said blade having X-, Y-, and Z-axes, said concave curve of said blade beginning at about 60% of the length from the first end thereof on said X-axis and turning into Z-axis and, thereafter, at about 80% of the length from the first end of said blade, said concave curve then also turning into the Y-axis, wherein the three axes of said concave curve of said blade thereby follow the anatomical curve of the nasal-maxillary junction, said blade also defining a plurality of cutting teeth along the entire length of the inferior Z-axis edge of said concave curve, said teeth having their cross-section in the XY plane.

2. The surgical saw as recited in claim 1 in which the mean angle of the Y-axis curvature of said blade with reference to the longitudinal X-axis of said blade is about 30 degrees.

3. The surgical blade as recited in claim 2 in which said blade comprises a Y plane thickness of about 0.5 mm, a Z plane width of about 4.0 mm, and an X axis length of about 30 mm.

4. The surgical saw as recited in claim 2 in which the superior edge of said concave curve of said blade has a smooth surface, wherein damage to soft tissue is thereby avoided.

5. The surgical saw as recited in claim 4 in which said shank extension comprises a solid cylindrical segment adapted to position said blade at an X-axis offset relative to a saw chuck.

* * * * *